(12) United States Patent
Zhang et al.

(10) Patent No.: US 9,366,610 B2
(45) Date of Patent: Jun. 14, 2016

(54) PORTABLE DIGITAL DISPLAY HARDNESS TESTER

(71) Applicant: Shenyang Tianxing Testing Instruments Co., LTD, Shenyang (CN)

(72) Inventors: Fenglin Zhang, Shenyang (CN); Dan Wu, Shenyang (CN); Liping Liu, Shenyang (CN); Luming Zhang, Shenyang (CN)

(73) Assignee: SHENYANG TIANXING TESTING INSTRUMENTS CO., LTD., Shenyang (CN)

( * ) Notice: Subject to any disclaimer, the term of this patent is extended or adjusted under 35 U.S.C. 154(b) by 155 days.

(21) Appl. No.: 14/345,879

(22) PCT Filed: Mar. 12, 2013

(86) PCT No.: PCT/CN2013/072446
§ 371 (c)(1),
(2) Date: Mar. 19, 2014

(87) PCT Pub. No.: WO2013/135162
PCT Pub. Date: Sep. 19, 2013

(65) Prior Publication Data
US 2014/0224003 A1 Aug. 14, 2014

(30) Foreign Application Priority Data
Mar. 12, 2013 (CN) .................. 2012 2 0091764 U (51) Int. Cl.
*G01N 3/42* (2006.01)
(52) U.S. Cl.
CPC .......... *G01N 3/42* (2013.01); *G01N 2203/0078* (2013.01); *G01N 2203/0206* (2013.01)
(58) Field of Classification Search
CPC ............ G01N 3/42; G01N 2203/0078; G01N 2203/0206
USPC ........................................................... 73/82
See application file for complete search history.

(56) References Cited

U.S. PATENT DOCUMENTS

| 2,448,645 A | 9/1948 | Williams |
| 2,466,567 A | 4/1949 | Williams |

(Continued)

FOREIGN PATENT DOCUMENTS

| CN | 1556387 A | 12/2004 |
| CN | 201191257 Y | 2/2009 |

(Continued)

OTHER PUBLICATIONS

International Search Report for PCT/CN2013/072446, Mailed Jun. 20, 2013.

*Primary Examiner* — Freddie Kirkland, III
(74) *Attorney, Agent, or Firm* — Smith, Gambrell & Russell, LLP (57) ABSTRACT

The invention relates to a material hardness testing instrument, specifically to a portable digital display hardness tester, comprising a magnetic chuck, a support, a force measuring device, an indenter, an electronic circuit board, a digital display, and a force applying and indentation depth measuring device consisting of a hand wheel, a rotary encoder and a micrometric screw pair. The support is equipped with the rotary encoder. The micrometric nut is installed in a hole. The digital display is located in the front. The support is fixed on the magnetic chuck. The micrometric nut is internally provided with the micrometric screw. The rotating shaft of the rotary encoder is connected with the micrometric screw and rotates along with the micrometric screw. The upper end of the micrometric screw is connected with the hand wheel, while the lower end is connected with the force measuring device. The lower end of the force measuring device is connected with the indenter. The hand wheel, the micrometric screw, the force measuring device and the indenter are connected and coaxial, capable of moving axially along with the rotation of the hand wheel. The invention is simply structured, convenient in reading, easy to operate, high in accuracy, capable of being applied to the onsite, quick hardness testing of large parts, and capable of testing the Brinell hardness and Vickers hardness through depth measurement.

15 Claims, 4 Drawing Sheets

(56) References Cited

U.S. PATENT DOCUMENTS

| | | | |
|---|---|---|---|
| 2,544,205 A | 3/1951 | Williams | |
| 3,389,597 A | 6/1968 | Williams | |
| 4,196,616 A * | 4/1980 | Argabrite | G01N 3/42 248/289.11 |
| 4,199,976 A * | 4/1980 | Edward | G01N 3/44 73/81 |
| 4,361,034 A * | 11/1982 | Borgersen | G01N 3/42 73/81 |
| 4,535,623 A * | 8/1985 | Gilberto | G01N 3/42 73/81 |
| 5,879,312 A * | 3/1999 | Imoto | A61B 5/0053 600/587 |
| 8,074,497 B2 * | 12/2011 | Sawa | G01N 3/42 73/81 |
| 8,590,367 B2 * | 11/2013 | Biddle | G01N 3/42 137/539.5 |

FOREIGN PATENT DOCUMENTS

| | | |
|---|---|---|
| CN | 201322709 Y | 10/2009 |
| CN | 202471531 U | 10/2012 |
| CN | 202486006 U | 10/2012 |
| JP | 2004037424 A | 2/2004 |

* cited by examiner

PORTABLE DIGITAL DISPLAY HARDNESS TESTER

FIELD OF THE INVENTION

The invention relates to a material hardness testing instrument, in particular to a portable digital display hardness tester.

BACKGROUND OF THE INVENTION

At present, the majority of the conventional hardness testers adopt the principle of applying stress statically and then measuring the indentation, wherein the Rockwell hardness tester measures the depth of the indentation and directly displays the hardness value; the Brinell hardness tester measures the diameter of the indentation, checks the table or calculates the hardness value; and the Vickers hardness tester measures the diagonal length of the indentation, checks the table or calculates the hardness value. Those meters are desktops and can only be used in labs to test middle and small parts. For a great number of parts produced on a production site, samples must be made or drawn and then sent to the labs to test the hardness. Therefore, those hardness testers have low working efficiency and cannot monitor the hardness of parts in real time on the production site. The Leeb hardness tester, which is quick and convenient but has low accuracy and poor reliability, is adopted for cases where sampling is not allowed and the hardness of the main body of the workpiece must be tested, in particular the weld joint hardness of key members such as the boilers, pressure containers, and pressure pipes. The test results obtained by the Leeb hardness tester shall be converted into a Rockwell, Brinell, or Vickers hardness value. The Leeb hardness tester adopts the rebound test method of dynamic application which is different from that of the Rockwell, Brinell, and Vickers hardness test, so the converted hardness value has a relatively large error.

Plants have an urgent need for a portable digital display hardness tester adopting the Rockwell, Brinell, and Vickers test principle. This hardness tester shall feature portability, simple operation, convenient reading, high efficiency, and high accuracy, and be preferably smart, capable of automatically calibrating the zero point, and automatically correcting the measured value.

An American patent, U.S. Pat. No. 2,544,205, disclosed on Mar. 6, 1951, describes a portable Rockwell hardness tester consisting of a hand wheel, a micrometric nut, a micrometric screw, a drum wheel, a U-shaped elastomer, a hardness indicating gauge, an indenter and a handle. The hand wheel applies test force; the micrometric nut and micrometric screw together with the drum wheel measure the depth of the indentation; the U-shaped elastomer and the hardness indicator gauge together realize the measurement of the test force; and the hardness value is read on the drum wheel.

An America patent, U.S. Pat. No. 2,466,567, disclosed on Apr. 5, 1949, an American patent, U.S. Pat. No. 3,389,597, disclosed on Jun. 25, 1968, and an American patent, U.S. Pat. No. 2,448,645, disclosed on Sep. 7, 1948, respectively describe a portable Rockwell hardness tester adopting similar principles.

The above mentioned patents are mainly applied to measurement of middle and small sized parts. The chain type hardness tester, U.S. Pat. No. 3,389,597, as shown in FIG. 4 can measure large cylindrical parts such as steel pipes and shafts, but the operation is very inconvenient and is usually executed by two persons in cooperation, one holding the tester and one mounting the chain. The hardness scale on the drum wheel is read through a transparent magnifying lens with a reading line. Each scale corresponding to the Rockwell hardness unit represents a 2 μm indentation depth delta value. Due to the distance between the amplifying lens and the drum wheel, the operator may obtain different hardness readings at different view viewing angles. The mentioned testers all have problems such as inconvenient operation, low efficiency, reading errors, failure or inconvenience to test large workpieces.

A Chinese utility model patent, publication number CN201322709Y and application number 200820231921.9, disclosed a portable hardness tester on Oct. 7, 2009. According to this utility model patent, the hardness tester is fixed on the surface of a test sample through two magnetic chucks. The hardness tester has an indentation depth measuring unit consisting of a micrometric nut, a micrometric screw and a reading drum wheel. A U-shaped elastic frame and an indicating gauge work together to indicate the testing force, and then the hardness value is read from the reading drum wheel. In this utility model patent, the hardness indication system is provided with a structure integrating a fixed scale indicator drum and a rotary reading scale drum wheel. Compared with the mentioned American patents, such drum wheel reading structure similar to the micrometer improves the indentation depth measuring accuracy and the hardness value reading accuracy and reduces artificial reading errors. However, this utility model patent still has the following disadvantages:

a. Complicated operation, and low efficiency: the complete test steps include: absorbing the workpiece, setting zero for the scales of the indicator gauge, applying the initial test force, setting zero for the reading drum wheel, applying the total test force, keeping the test force, reducing the test force to the initial test force, reading the hardness value on the drum wheel, and unloading all testing force;

b. Inconvenient reading, low reading accuracy, and operator's reading errors: it is required to carefully operate the drum wheel and read the hardness value represented by the scale on the drum wheel;

c. Low resolution of the displacement measurement and force measurement, low accuracy, and operator's reading errors;

d. Failure to calibrate the hardness value: when the instrument is used, the hardness readings have errors once the U-shaped elastomer undergoes slight deformation or the indicator gauge is impacted, thereby causing measuring errors; in such circumstances, the indicator gauge must be returned to the manufacturer for calibration, and the user cannot calibrate the instrument; and, e. Low efficiency of the Brinell hardness test, and operator's reading errors: The instrument can only make an indentation on the test sample, and then the user is required to read the indentation diameter with a reading microscope and check the table to obtain the Brinell hardness value. It costs several minutes to complete one test.

A Chinese utility model patent, publication number CN1556387A, application number 200410012621.8, disclosed a portable digital display magnetic hardness tester on Dec. 22, 2004. This utility model patent adopts a case structure containing all main parts. A worm-and-gear structure is adopted to apply the testing force; a main shaft for applying the force is equipped with a displacement sensor for measuring the indentation depth; three force sensors are adopted, and the sum of outputs of those three force sensors represents the testing force; a computer calculates and displays the hardness value after receiving signals from the sensors through electronic circuits. This utility model patent also has the following disadvantages:

a. Complicated structure, big weight, and non-portability.

b. Inconvenient operation, and impractical. Regarding the instrument involved in the utility model patent, the locking hand wheels on both sides are required to be loosened to drop the case rack and then locked each time before testing, operated by two hands to apply the force during the test, and loosened again to support the rack and then fix the rack at the completion of the test. Such complicated working mode is very unacceptable for the operators.

c. Three force sensors are adopted, resulting in high cost.

d. A specific technical solution for the Brinell hardness and Vickers hardness testing is required. Actually, testing of the Brinell hardness and Vickers hardness has higher requirements on the instrument in the aspect of force measuring accuracy, indentation depth measuring accuracy, resolution, and repeatability. Usually, common displacement sensors have difficulties to meet the corresponding requirements.

China Standard GB/T24523-2009 stipulates an advanced Brinell hardness test method: quick indentation (Brinell) hardness test method for metal material. This is the depth measurement of Brinell hardness test, also applicable to the Vickers hardness testing. The principle is as follows:

Apply a certain testing force (including a initial test force and a working test force) to a cemented carbide ball with a certain diameter to press the ball into the surface of the test sample, keep a regulated time, release the working test force, and measure the difference value (depth value) of positions of the indenter before applying and after releasing the working test force on condition of the primary testing force. Measure the corresponding depth values of a plurality of standard Brinell hard blocks, and obtain a relation curve of the indentation depth and the Brinell hardness on certain testing conditions according to the Brinell hardness value and the depth value. When measuring the hardness, check the depth value measured by the hardness tester against the relation curve of the indentation depth and the Brinell hardness to obtain the Brinell hardness value of this material.

Compared with the traditional Brinell hardness test method, this method is an important technical progress. It can realize the quick testing and direct reading of the Brinell hardness, has no need for optical microscopes with a use history of more than 100 years, avoids artificial reading errors, solves the problems in the onsite quick Brinell hardness test of batches of products during production, and even realizes online automatic hardness testing of batches of products in workshops.

The depth-measuring Brinell hardness and Vickers hardness test is a new technique only adopted by some overseas desktop machines. It has not been found in the portable hardness testers yet. The main technical difficulties lie in the simple, light, and small structure of the portable hardness tester, limited inner space, and installation of the common high-accuracy displacement sensor. In addition, it is not economical to install the high-accuracy displacement sensor on a portable hardness tester.

According to the regulations of the related standard, the Brinell hardness measuring scope is 8~650 HBW; the common scale for the hardness Brinell hardness tester is a 2.5 mm ball and 187.5 kg force; and for a test sample with a hardness value of 650 HBW, the minimum indentation depth is only 0.0365 mm.

The highlight of the portable Vickers hardness tester is the accurate measurement of the hardness of the nitriding layers on large work pieces such as dies and shafts. In the prior art, accurate testing of the hardness of the nitriding layers on large work pieces has been a challenge because the nitriding layers are thin but hard, with a thickness of 0.1~0.4 mm and a hardness of over 1,000 HV5, and cannot be applied with a large test force. For the 1,000 HV5 nitriding layer, the 5 kg test force is employed, and the indentation depth is only 0.0143 mm. The depth-measurement targets at the depth difference of the indentation, so this numerical value is small.

Realizing high-accuracy and high-resolution displacement measurement on the portable hardness tester is a key for making Brinell and Vickers hardness tests. The inductive displacement transducer and grating displacement transducer usually adopted in the hardness tester field have difficulty meeting the mentioned requirements. Therefore, depth-measuring Brinell and Vickers hardness testing methods have not been applied to portable hardness testers yet.

If such method is realized on a portable hardness tester, the accurate testing of the main body hardness of many key, large, industrial parts becomes possible, making progress in the quality management of the related products.

BRIEF SUMMARY OF THE INVENTION

The objective of the invention is to provide a portable digital display hardness tester. This hardness tester features portability, simple structure, convenience in operation and reading, and high accuracy, and it can realize high-accuracy, smart testing, automatic zero calibration and automatic measuring value calibration. It tests the Rockwell hardness, and realize onsite quick testing of the Brinell hardness and Vickers hardness through depth measurement, and it can replace the currently common, low-accuracy Leeb hardness tester.

The objective of the present invention is realized by the following technical scheme:

The invention comprises a support, a force measuring device, an indenter, an electronic circuit board, a digital display, a magnetic chuck, and a force applying and indentation depth measuring device. The force applying and indentation depth measuring device comprises a hand wheel, a rotary encoder and a micrometric screw pair consisting of a micrometric nut and a micrometric screw, wherein the micrometric nut is installed in the support; the micrometric screw is in threaded connection with the micrometric nut; one end of the micrometric screw is connected with the hand wheel, while the other end is connected with the force measuring device. The rotary encoder is installed on the support. The rotating shaft of the rotary encoder and the micrometric screw rotate synchronously. The indenter is installed on the force measuring device, together with the force measuring device and the micrometric screw axially moving up and down through the rotation of the hand wheel. One or both sides of the support are equipped with magnetic chucks for sucking test samples. The electronic circuit board is arranged above the magnetic chuck. The digital display is installed on the support or the magnetic chuck. The rotary encoder, the digital display and the force sensor in the force measuring device are electrically connected to the electronic circuit board. The displacement of the micrometric screw is measured by the rotary encoder.

Wherein, one end of the micrometric screw is connected with the hand wheel through a sleeve, and the other and of the micrometric screw is opened with a key groove; the key groove is internally equipped with a third key; and the micrometric screw rotates synchronously with the sleeve through the third key. The rotating shaft of the rotary encoder is connected with the micrometric screw through the sleeve, and rotates synchronously with the micrometric screw. One end of the sleeve is fixed in the inner hole of the hand wheel, while the other end is inserted into the centre hole of the rotating shaft of the rotary encoder, and the micrometric screw is located in the sleeve. The outer surface of the sleeve is opened with a first axial groove along the axial direction. The upper edge of the rotating shaft of the rotary encoder is provided with a second key. The rotating shaft of the rotary encoder is connected with the sleeve through the second key. The second key slides in the first axial groove during movement of the micrometric screw. The support is internally opened with a hole along the axial direction. The micrometric nut is installed in the hole of the support. One end of the micrometric nut is provided with external conical screw threads. A plurality of second axial grooves is uniformly distributed on the external conical screw threads along the circumference. The external conical screw threads are in threaded connection with a conical nut for regulating the degree of the tightness fit of the micrometric screw pair. The force measuring device comprises a sliding bushing, a force sensor and a force sensor seat, wherein one end of the sliding bushing is connected with the other end of the micrometric screw, and the other end of the sliding bushing is connected with one end of the force sensor; the force sensor seat is installed at the bottom of the other end of the force sensor. The indenter is connected to the lower end of the force sensor seat. The force sensor seat is provided with an illumination circuit board. The illumination circuit board is located above the indenter and provided with an LED light. One end of the sliding bushing is connected with the other end of the micrometric screw through a pressing cap and two semi-rings, and a steel ball is located between the end face of other end of the micrometric screw and the sliding bushing. The outer surface of the sliding bushing is circumferentially opened with a third axial groove. A first key is installed on the micrometric nut and slides in the third axial groove. The sliding bushing, the force sensor, the force sensor seat, the indenter, the micrometric screw, the micrometric nut, the rotating shaft of the rotary encoder, the hand wheel and the axial hole in the support are coaxial. The hardness tester is provided with a handle. The handle is installed on the two sides of the support through a connecting board, or installed on the magnetic chuck. The magnetic chuck comprises a stator containing permanent magnets, a rotor containing permanent magnets, a magnetic switch lever and a cam, wherein the rotor is installed in the stator; the cam is installed on the rotor shaft of the rotor; the magnetic switch lever is connected with the rotor shaft through the hole on the cam; and the cam rotates along with the magnetic switch lever.

The invention has the following advantages and beneficial effects:

1. The hardness tester of the invention is the first to use the combination of the micrometric nut, the micrometric screw and the rotary encoder as the indentation depth measuring device, realizing the high-resolution and high-accuracy indentation depth measurement and taking economy into consideration.

2. The invention is the first to realize the quick Brinell hardness and Vickers hardness test on a portable hardness tester through depth measuring and realize direct display, so the onsite, quick, accurate testing of the hardness of large workpieces becomes possible. This invention can be used to test batches of workpieces one by one on the site of the plant and can replace the low-accuracy Leeb hardness tester.

3. The invention is simply structured, light, convenient, and portable.

4. The invention realizes simple testing operation. The operator can complete the test in several to dozens of seconds by several simple operations including applying the force, keeping the force, releasing the force, and reading.

5. The invention automatically calibrates the zero point of the force value after being started, avoiding errors caused by temperature excursion or time excursion of the sensor and the electronic circuit.

6. The invention can correct the measuring values of the instrument through the standard hardness block, so the instrument can still keep high accuracy after use for a long time.

Wherein: 1. magnetic switch lever; 2. cam; 3. magnetic chuck; 4. handle; 5. digital display; 6. display screen; 7. key; 8. locking screw; 9. hand wheel; 10. sleeve; 11. conical nut; 12. rotating shaft of the rotary encoder; 13. micrometric screw; 14. micrometric nut; 15. connecting plate; 16. first key; 17. battery pack; 18. rotor shaft; 19. stator; 20. rotor; 21. force sensor; 22. force sensor seat; 23. illumination circuit board; 24. indenter; 25. LED light; 26. test sample; 27. electronic circuit board; 28. sliding bushing; 29. steel ball; 30. semiring; 31. pressing cap; 32. support; 33. rotary encoder; 34. the second key; 35. the third key; 36. measuring circuit; 37. CPU circuit; 38. power circuit.

DETAILED DESCRIPTION OF THE INVENTION

The invention is described in further detail with reference to the attached drawings.

Figure 1:
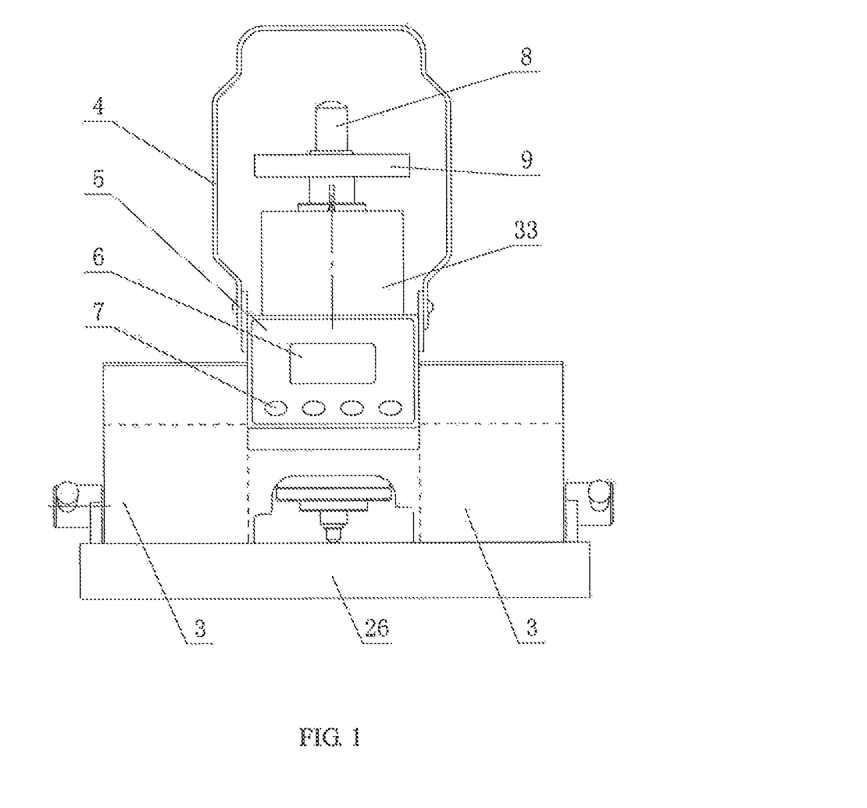
FIG. 1 is a schematic view of the external structure of the invention.
Figure 2:
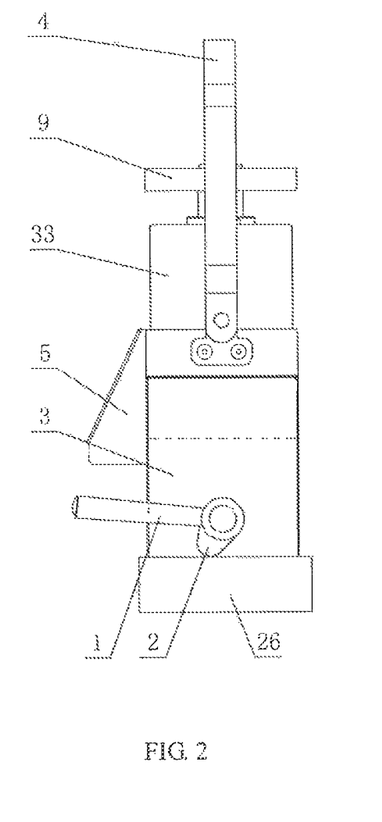
FIG. 2 is a right view of FIG. 1.
Figure 3:
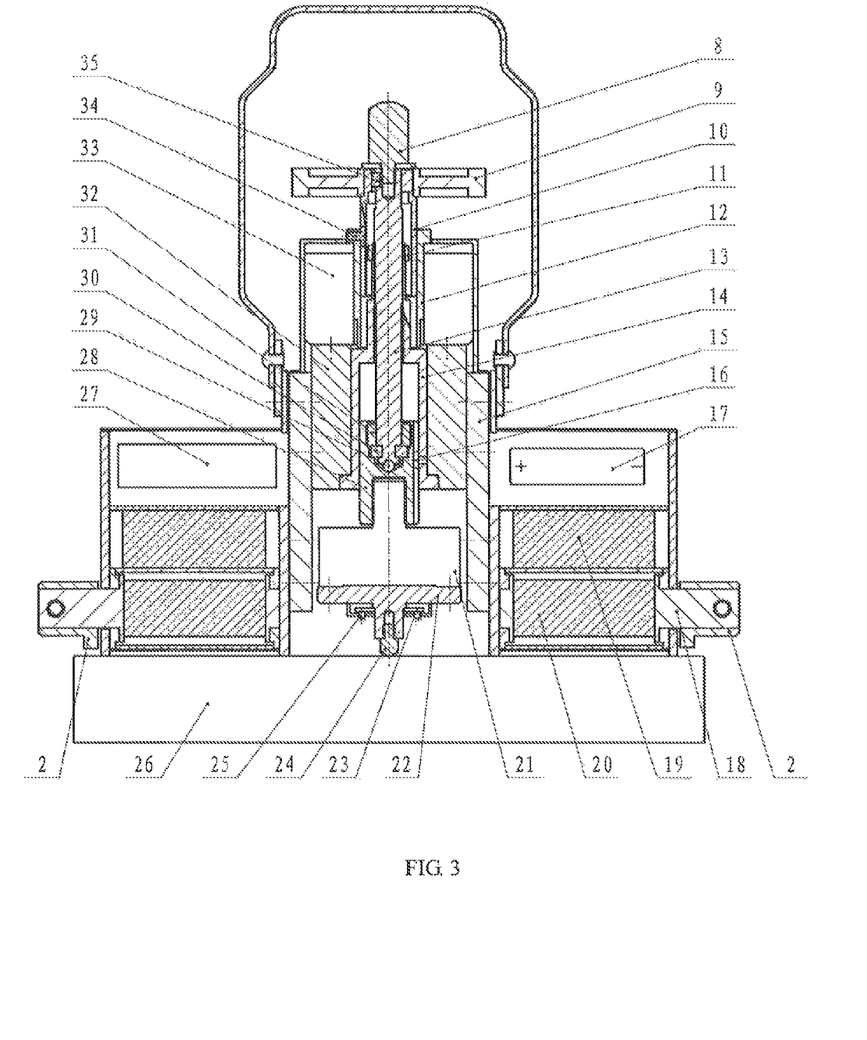
FIG. 3 is a schematic view of the internal structure of the invention.

As shown in FIGS. 1-3, the invention comprises support 32, force measuring device, indenter 24, electronic circuit board 27, digital display 5, magnetic, chuck 3 and force applying and indentation depth measuring device, wherein the force applying and indentation depth measuring device comprises hand wheel 9, rotary encoder 33, sleeve 10 and micrometric screw pair consisting of a micrometric nut 14 and micrometric screw 13. The force measuring device comprises sliding bushing 28, force sensor 21 and force sensor seat 22.

The support 32 is a main bracket, internally opened with a round hole along the axial direction. The micrometric nut 14 is installed in the round hole of the support 32. The micrometric screw 13 is located in the micrometric nut 14, in threaded connection with the micrometric nut 14. One end (upper end) of the micrometric screw 13 is connected with sleeve 10. The sleeve 10 is fixed in the inner hole of the hand wheel 9, and one end of the micrometric screw 13 is opened with a key groove. The key groove is internally equipped with the third key 35. The micrometric screw 13 keeps rotating synchronously with the hand wheel 10 and the hand wheel 9 through the third key 35. One end portion of the micrometric screw 13 is fastened by locking screw 8, and the other end (lower end) of the micrometric screw 13 is connected with the force sensor 21 through the sliding hushing 28. One end (upper end) of the micrometric nut 14 is located between the sleeve 10 and the micrometric screw 13, and one end of the micrometric nut 14 is provided with external conical screw threads. A plurality of second axial grooves (three in this embodiment) are uniformly distributed on the external conical screw threads along the circumference. The external conical screw threads are in threaded connection with a conical nut 11. The clearance fit of the micrometric screw pair can be regulated through the conical nut 11.

The rotary encoder 33 is installed on the support 32. The rotating shaft 12 of the rotary encoder is coaxial to the micrometric screw pair. One end of the sleeve 10 is fixedly connected in the internal hole of the hand wheel 9, and the other end is inserted into the centre hole of the rotating shaft 12 of the rotary encoder. The outer surface of the sleeve 10 is axially opened with a first groove. The upper end of the rotating shaft 12 of the rotary encoder is provided with second key 34. The rotating shaft 12 of the rotary encoder is connected with the sleeve 10 through the second key 34. The second key 34 can slide in the first axial groove during movement of the micrometric screw 13. The rotating shaft 12 of the rotary encoder is connected with the micrometric screw 13 through the sleeve 10, and rotates synchronously with the micrometric screw 13.

Figure 4:
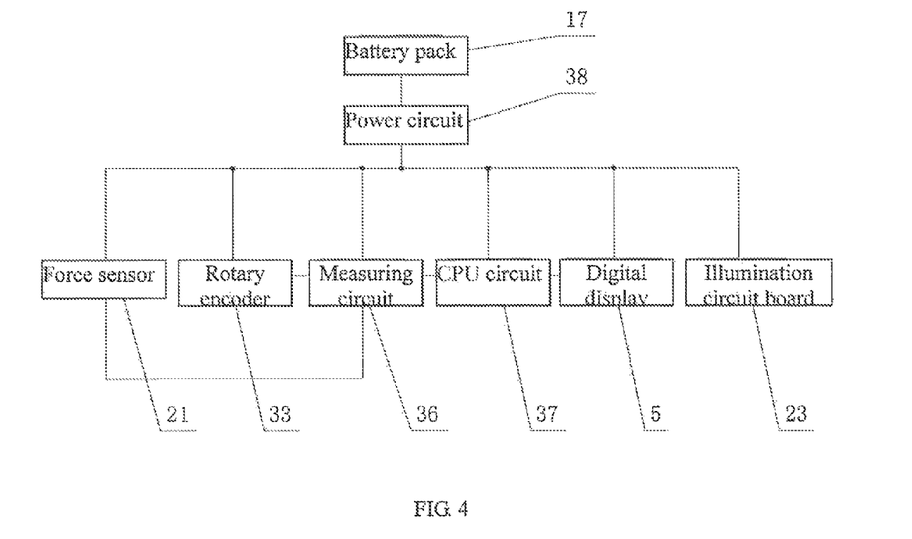
FIG. 4 is an electrical electronic block diagram of the invention.

When the hand wheel 9 is rotated, the rotating shaft 12 of the rotary encoder, the sleeve 10 and the micrometric screw 13 rotate synchronously and the micrometric screw 13 axially moves up and down. Each cycle the hand wheel 9 rotates, the micrometric screw 13 axially moves by a screw pitch. The rotary encoder 33 divides this displacement into several thousands of scales and transmits the signal to a CPU circuit 37 through a measuring circuit 36 so as to realize accurate measurement of the indentation depth. In this embodiment, one screw pitch is 0.5 mm. In the process of testing the Rockwell hardness, the rotating shaft 12 of the rotary encoder can output 5,000 scales in each cycle of rotation, and each scale represents 0.1 μm displacement, equivalent to 0.05 Rockwell hardness unit. When the depth measurement is adopted to test the Brinell hardness and Vickers hardness, the rotating shaft 12 of the rotary encoder can output 10,000 scales in each cycle of rotation by means of the frequency division technology, and each scales represents 0.05 μm displacement, equivalent to 1/730 of the minimum indentation depth (the hardness value of the quenched steel is 650 HBW) for the Brinell hardness HBW 2.5/187.5 scale and equivalent to 1/280 of the minimum indentation depth (the hardness value of the nitriding layer is 1,000 HV5) for the Vickers hardness HV5 scale. The requirements of the related standards GB/T230.2, GB/T231.2 and GB/T4340 can be met.

One end (upper end) of the sliding bushing 28 is connected with the other end (lower end) of the micrometric screw 13 through a pressing cap 31 and two semi-rings 30, and the other end (lower end) of the sliding bushing 28 is in threaded connection with one end (upper end) of the force sensor 21. The force sensor 22 is installed at the bottom of the other end (lower end) of the force sensor 21. The indenter 24 is connected to the lower end of the force sensor seat 22. The indenter 24 may be a ball indenter, or a diamond indenter. A steel ball 29 is located between the other end of the micrometric screw 13 and the sliding bushing 28, and the end face of the other end of the micrometric screw 13 is provided with a spherical recess adapted to the steel ball 29 and matched with the steel ball 29. The outer surface of the sliding bushing 28 is opened with a third axial groove along the circumference. The micrometric nut 14 is installed with a first key 16. The first key 16 slides in the third axial groove. The sliding bushing 28 only moves axially in the micrometric nut 14 with the guidance of the first key 16, avoiding rotation of the whole force measuring device and the indenter 24. The steel ball 29 can effectively eliminate the transverse action force on the sliding bushing 28 and the first key 16 when the micrometric screw 13 rotates. An illumination circuit board 23 is installed below the force sensor seat 22. The illumination circuit board 23 is provided with LED light 25. During test, the LED light 25 can light the testing area such that the operator conveniently selects the test point and observe the whole testing process.

In this invention, the sliding bushing 28, the force sensor 21, the force sensor seat 22, the indenter 24, the micrometric screw 13, the micrometric nut 14, the rotating shaft 12 of the rotary encoder, the hand wheel 9, the sleeve 10 and the axial round hole in the support 32 all are coaxial. The hand wheel 9 of the invention can be replaced by an electric motor. The output shaft of the motor is connected with the sleeve 10, and the motor drives the sleeve 10, the micrometric screw 13 and the rotating shaft 12 of the rotary encoder to rotate.

A digital display 5 is installed in the front of the support 32. The digital display 5 comprises a display screen 6 and key 7, wherein the display screen 6 is inclined to the support 32 to facilitate observation during operation. The digital display 5 can also be installed above the magnetic chuck 3. The electronic circuit board 27 is installed above the magnetic chuck 3. The rotary encoder 33, the digital display 5, the illumination circuit board 23 and the force sensor 21 are respectively electrically connected with the electronic circuit board 27.

The electronic circuit board 27 comprises the measuring circuit 36, the CPU circuit 37 and the power circuit 38. The input of the measuring circuit 36 is connected to the rotary encoder 33 and the force sensor 21, while the output is connected to the CPU circuit 37 which is also connected with the digital display 5. The force sensor 21 and the rotary encoder 33 respectively transmit the force and displacement signals to the CPU circuit 37 through the measuring circuit 36. The digital display 5 displays the testing force value and the measured hardness value after the CPU circuit 37 processes the force and the displacement signals. The electronic circuit board 27 can automatically calibrate zero for the force value. After the tester is powered on, the CPU circuit 37 automatically collects the zero output signal of the force sensor 21, and displays the force value on the digital display 5 after reducing the output signal of the force sensor 21 by the zero value when applying the force.

The invention is also provided with a handle 4. The handle 4 is installed on the two sides of the support 32 through a connecting plate 15, or installed on the magnetic chuck 3 to facilitate lifting of the hardness tester.

The magnetic chuck 3 comprises a stator 19 containing a permanent magnet, a rotor 20 containing a permanent magnet, a magnetic switch lever 1 and a cam 2, wherein the rotor 20 is installed in the stator 19; the cam 2 is installed on the rotor shaft 18 of the rotor 20; and the magnetic switch lever 1 is connected with the rotor shaft 18 through the hole on the cam 2. The magnetic suction 3 can suck or release the test sample 26 through pulling the magnetic switch lever 1, and the cam 2 can rotate along with the magnetic switch lever 1. When the magnetic switch lever 1 is pulled to control the magnetic chuck 3 to release the test sample 26, the steel/or iron metal test sample 26 may still be sucked together with the magnetic chuck 3 due to a small amount of residual magnetism. In such circumstances, the magnetic switch lever 1 can be pulled continuously until the cam 2 protrudes out of the bottom plane of the magnetic chuck 3, and then the test sample 26 and the magnetic chuck 3 can be separated by the lever effect.

In this embodiment, two magnetic chuck 3 are adopted, symmetrically installed on two sides of the support 32. One magnetic chuck can be used to test the small workpieces, and three magnetic chucks can be used to test the right-angle weld joint of the round pipes.

According to the requirements of the depth-measuring Brinell hardness test standard GB/T24523-2009, the tester is required to test a series of standard Brinell hard blocks before delivery, and the tested hardness values shall be input into the tester to establish a hardness-indentation depth curve. The same work shall also been done when the depth measurement is adopted to test the Vickers hardness.

The working principle of the invention is as follows:

Place the invention on the test sample 26, pull the magnetic switch lever 1 such that the magnetic chucks 3 are attracted to suck the test sample 26; rotate the hand wheel 9 to drive the sleeve 10, the micrometric screw 13 and the rotating shaft 12 of the rotary encoder to rotate synchronously, and then the micrometric screw 13 pushes the force sensor 21, the force sensor seat 22 and the indenter 24 to move downward to the test sample 26 through the steel ball 29 and the sliding bushing 28; when the indenter 24 contacts with the test sample 26, the top end of the indenter 24 is pressed into the test sample along with the continuous rotation of the hand wheel 9 to generate pressure marks on the surface of the test sample 26. During the test, the force sensor 21 monitors the testing force on the indenter 24 in real time, and transmits signals to the CPU circuit 37. When the testing force reaches a regulated primary testing force value, the CPU circuit 37 records the indentation depth value at this moment, continuously applies a force to reach the total testing force value, stops applying the force and then holds for a regulated time. Rotate the hand wheel 9 reversely, the CPU circuit 37 records the pressure mark depth value at this moment when the testing force is reduced to the regulated primary testing force value, processes and calculates the difference of indentation depths by the action of the primary testing force before and after applying the total testing force, and displays the hardness value on the test sample 26 on the display screen 6. After completing the test, push the magnetic switch lever 1 such that the magnetic chucks 3 separate from the test sample 26. It only costs several or dozens of seconds to complete the whole test.

In the most preferable embodiment of this invention, the testing operation process can be simplified to the following steps:

Sucking the test sample, applying the total test force, keeping the test force, releasing the total test force, reading the hardness value, and releasing the test sample.

What is claimed is:

1. A portable digital display hardness tester, comprising a support, a force measuring device, an indenter, an electronic circuit board, a digital display, a magnetic chuck, and a force applying and indentation depth measuring device wherein: the force applying and indentation depth measuring device comprises a hand wheel (9), a rotary encoder (33) and a micrometric screw pair consisting of a micrometric nut (14) and a micrometric screw (13), wherein the micrometric nut (14) is installed in the support (32); the micrometric screw (13) is in threaded connection with the micrometric nut (14); one end of the micrometric screw (13) is connected with the hand wheel (9), while the other end is connected with the force measuring device; the rotary encoder (33) is installed on the support (32); the rotating shaft (12) of the rotary encoder and the micrometric screw (13) rotate synchronously; the indenter (24) is installed on the force measuring device, together with the force measuring device and the micrometric screw (13) axially moving up and down through the rotation of the hand wheel (9); the support (32) is equipped with the magnetic chuck (3) for sucking a test sample (26); the electronic circuit board (27) is arranged above the magnetic chuck (3); the digital display (5) is installed on the support (32) or the magnetic chuck (3); the rotary encoder (33), the digital display (5) and the force sensor in the force measuring device are respectively electrically connected to the electronic circuit board (27); and the displacement of the micrometric screw (13) is measured by the rotary encoder (33).

2. The portable digital display hardness tester according to claim 1, wherein: one end of the micrometric screw (13) is connected with the hand wheel (9) through a sleeve (10), while one end of the micrometric screw (13) is opened with a key groove; the key groove is internally equipped with a third key (35); the micrometric screw (13) rotates synchronously to the sleeve (10) through the third key (35); the rotating shaft (12) of the rotary encoder is connected with the micrometric screw (13) through the sleeve (10) and rotates synchronously to the micrometric screw (13).

3. The portable digital display hardness tester according to claim 2, wherein: one end of the sleeve (10) is fixedly connected in an inner hole of the hand wheel (9), while the other end is inserted in the centre hole of the rotating shaft (12) of the rotary encoder, the micrometric screw (13) is located in the sleeve (10); the outer surface of the sleeve (10) is axially opened with a first axial groove; the upper end of the rotating shaft (12) of the rotary encoder is provided with a second key (34); the rotating shaft (12) of the rotary encoder is connected with the sleeve (10) through the second key (34); and the second key (34) slides in the first axial groove during movement of the micrometric screw (13).

4. The portable digital display hardness tester according to claim 1, wherein: the support (32) is internally opened with a hole along the axial direction; the micrometric nut (14) is installed in the hole of the support (32); one end of the micrometric nut (14) is provided with external conical screw threads; a plurality of second axial grooves are uniformly on the external conical screw threads along the circumference; and the external conical screw threads are in threaded connection with a conical nut (11) for regulating the degree of tightness fit of the micrometric screw pair.

5. The portable digital display hardness tester according to claim 1, wherein: the force measuring device comprises a sliding bushing (28), a force sensor (21) and a force sensor seat (22), wherein one end of the sliding bushing (28) is connected with the other end of the micrometric screw (13); the other end of the sliding bushing (28) is connected with one end of the force sensor (21); the force sensor seat (22) is installed at the bottom of the other end of the force sensor (21); and the indenter (24) is connected to the lower end of the force sensor seat (22).

6. The portable digital display hardness tester according to claim 5, wherein: the force sensor seat (22) is provided with an illumination circuit board (23); and the illumination circuit board (23) is located above the indenter (24) and is provided with an LED light (25).

7. The portable digital display hardness tester according to claim 5, wherein: one end of the sliding bushing (28) is connected with the other end of the micrometric screw (13) through a pressing cap (31) and two semi-rings (30); a steel ball (29) is located between the end face of the other end of the micrometric screw (13) and the sliding bushing (28); the external surface of the sliding bushing (28) is opened with a third axial groove along the circumference; the micrometric nut (14) is installed with a first key (16); and the first key (16) slides in the third axial groove.

8. The portable digital display hardness tester according to claim 5, wherein: the sliding bushing (28), the force sensor (21), the force sensor seat (22), the indenter (24), the micrometric screw (13), the micrometric nut (14), the rotating shaft (12) of the rotary encoder, the hand wheel (9), and the axial hole in the support (32) are coaxial.

9. The portable digital display hardness tester according to claim 1, wherein: the hardness tester is provided with a handle (4); the handle (4) is installed on both sides of the support (32), or installed on the magnetic chuck (3) through a connecting plate (15).

10. The portable digital display hardness tester according to claim 1, wherein: the magnetic chuck (3) comprises a stator (19) containing a permanent magnet, a rotor (20) containing a permanent magnet, a magnetic switch lever (1) and a cam (2), wherein the rotor (20) is installed in the stator (19); the cam (2) is installed on the rotor shaft (18) of the rotor (20); the magnetic switch lever (1) is connected with the rotor shaft (18) through the hole on the cam (2); and the cam (2) rotates along with the magnetic switch lever (1).

11. The portable digital display hardness tester of claim 1 wherein there are multiple magnetic chucks for attachment of the portable digital display hardness tester to the test sample.

12. A portable digital display hardness tester, comprising a support, a force measuring device, an indenter, an electronic circuit board, a digital display, a magnetic chuck, and a force applying and indentation depth measuring device wherein: the force applying and indentation depth measuring device comprises a driver (9), a rotary encoder (33) and a micrometric screw pair consisting of a micrometric nut (14) and a micrometric screw (13), wherein the micrometric nut (14) is installed in the support (32); the micrometric screw (13) is in threaded connection with the micrometric nut (14); one end of the micrometric screw (13) is connected with the driver (9), while the other end is connected with the force measuring device; the rotary encoder (33) is installed on the support (32); the rotating shaft (12) of the rotary encoder and the micrometric screw (13) rotate synchronously; the indenter (24) is installed on the force measuring device, together with the force measuring device and the micrometric screw (13) axially moving up and down through the rotation of the driver (9); the support (32) is equipped with the magnetic chuck (3) for sucking a test sample (26); the rotary encoder (33), the digital display (5) and the force sensor in the force measuring device are respectively electrically connected to the electronic circuit board (27); and the displacement of the micrometric screw (13) is measured by the rotary encoder (33).

13. The portable digital display hardness tester of claim 12 wherein the driver is a hand wheel (9).

14. The portable digital display hardness tester of claim 12 wherein the electronic circuit board (27) is arranged above the magnetic chuck (3).

15. The portable digital display hardness tester of claim 12 wherein the digital display (5) is installed on the support (32) or the magnetic chuck (3).

* * * * *